(12) United States Patent
Duckert et al.

(10) Patent No.: US 7,855,650 B2
(45) Date of Patent: Dec. 21, 2010

(54) SYSTEM AND METHOD FOR MONITORING THE COGNITIVE ABILITY OF A PERSON

(75) Inventors: David Duckert, Menomonee Falls, WI (US); Michael Beyerle, Pewee Valley, KY (US); Paul Cuddihy, Ballston Lake, NY (US); Vrinda Rajiv, Schenectady, NY (US)

(73) Assignee: The General Electric Company, Schenectady, NY (US)

( * ) Notice: Subject to any disclaimer, the term of this patent is extended or adjusted under 35 U.S.C. 154(b) by 339 days.

(21) Appl. No.: 12/103,275

(22) Filed: Apr. 15, 2008

(65) Prior Publication Data

US 2009/0256710 A1    Oct. 15, 2009

(51) Int. Cl.
    *G08B 23/00*    (2006.01)
(52) U.S. Cl. .................. 340/573.1; 340/506; 340/568.1; 340/539.11
(58) Field of Classification Search ............... 340/573.1, 340/506, 501, 539.1, 521–522, 517, 539.11, 340/523, 584, 541, 551, 568.1, 571, 572.1
See application file for complete search history.

(56) References Cited

U.S. PATENT DOCUMENTS

| | | | | |
|---|---|---|---|---|
| 4,259,548 A * | 3/1981 | Fahey et al. | .................. | 379/38 |
| 5,905,436 A * | 5/1999 | Dwight et al. | ........... | 340/573.1 |
| 6,032,035 A * | 2/2000 | Webster et al. | ........... | 455/404.2 |
| 6,211,791 B1 * | 4/2001 | Ponce de Leon et al. | .... | 340/601 |
| 6,611,206 B2 * | 8/2003 | Eshelman et al. | ........ | 340/573.1 |
| 6,796,799 B1 | 9/2004 | Yoshiike et al. | | |
| 7,091,865 B2 | 8/2006 | Cuddihy et al. | | |
| 7,154,399 B2 | 12/2006 | Cuddihy et al. | | |
| 7,228,203 B2 * | 6/2007 | Koselka et al. | ............... | 700/245 |
| 7,710,824 B1 * | 5/2010 | Katzer et al. | ................... | 367/99 |
| 2003/0117279 A1 | 6/2003 | Ueno et al. | | |
| 2003/0229471 A1 | 12/2003 | Guralnik et al. | | |
| 2005/0137465 A1 | 6/2005 | Cuddihy et al. | | |
| 2005/0181771 A1 * | 8/2005 | Cuddihy et al. | .......... | 455/414.1 |
| 2005/0234310 A1 | 10/2005 | Alwan et al. | | |
| 2007/0124466 A1 | 5/2007 | Brown | | |

FOREIGN PATENT DOCUMENTS

| | | |
|---|---|---|
| EP | 1034734 A1 | 9/2000 |
| GB | 2443274 A | 4/2008 |
| GB | 2455336 A | 6/2009 |
| WO | WO2005066909 A2 | 7/2005 |

OTHER PUBLICATIONS

Modie, Jonathan; OHSU Studies of Technology for Healthy Aging Get Boost; Oregon Health & Science University; Jan. 24, 2007.

* cited by examiner

*Primary Examiner*—Daniel Previl
(74) *Attorney, Agent, or Firm*—Andrus, Sceales, Starke & Sawall, LLP (57) ABSTRACT

A system and method for monitoring the health of a remotely located person is disclosed herein. The system includes at least one electronic device. The electronic device includes a first sensor a processor and a transmitter. The system also includes a remote monitoring station that receives data from at least one electronic device and produces an evaluation of the person's health.

20 Claims, 4 Drawing Sheets

SYSTEM AND METHOD FOR MONITORING THE COGNITIVE ABILITY OF A PERSON

FIELD OF THE DISCLOSURE

The present disclosure is related to the field of wellness monitoring. More specifically, the present disclosure is related to the remote monitoring of a person in order to monitor the person's cognitive abilities.

BACKGROUND

The populus in the Western civilization is now living longer due to medical advancements and increased attention to preventative medicine. For example, the number of elderly persons residing in the United States is increasing, and with the advancing age of the Baby Boomer generation, the number of elderly persons in the United States will increase significantly over the next several decades. Additionally, increased awareness and understanding of various mental and physical disabilities has led to an increase in the number of persons having diminished mental and/or physical faculties living independently.

With the increase in elderly and disabled persons living independently has come anxiety that these elderly and disabled persons are safe and secure in their own residences. There is increased anxiety by the elderly and disabled living alone that they may become injured or incapacitated and be unable to summon assistance. That anxiety is often shared by loved ones living at a distance from the elderly and/or disabled living independently.

Currently, the anxiety felt by the elderly and disabled living alone, as well as the anxiety felt by their loved ones, is addressed through several avenues. One way to ease anxiety is through frequent visits to the home by a caregiver. Such visits can be intrusive, time consuming, and often inconvenient or not appreciated. Another way is for the elderly or disabled person to move out of the home and move into a facility better able to monitor his or her health. This, however, strips the person of his or her independence, is costly and is often unwelcome. Another way to monitor the elderly or disabled persons is through technological assistance or monitoring of the person in the home.

Such technological systems that assist persons in their home include personal emergency response systems. In these systems, the elderly or disabled individual wears a watch, pendant, or other similar device and presses a button in the event of an emergency, such as a fall. The depressed button enables an alarm signal that is transmitted to a central monitoring facility that provides assistance by responding to the alarm signal and calls the individual to identify the problem. The facility can also initiate emergency communications to a predetermined list of contacts, such as relatives, neighbors, or emergency services, as required by the context of the situation. While a valuable service, these systems only identify problems that occur when the individual is able to press the emergency button.

Some known in-home monitoring systems attempt to detect unusual activity, such as, for example, an abnormally long "quiet period" within the house by arbitrarily choosing "daytime" and "nighttime" perimeters and sending an alert if there is no activity for a predetermined amount of time during the "daytime" time period. These known in-home monitoring systems provide the resident with a button which can be pressed to indicate whether the resident is home or is away. Such known systems often fail to accurately reflect real activity patterns of the resident. Further, the resident's responsibility to indicate whether he or she is in the house or away often goes unfulfilled, leading to a high false alert rate and low sensitivity for such known systems.

While the above-mentioned systems may provide the ability to monitor a person in order to respond to an emergency situation, these systems fail to collect any additional person diagnostic information from the implementation of such a monitoring system.

BRIEF DISCLOSURE

Both a system for and a method of monitoring a person using at least one sensor at location are herein disclosed.

In one embodiment of the system, the system includes at least one electronic device and a remote monitoring station that receives data from the at least one electronic device, stores the data, and analyzes the data to produce a health evaluation. In this embodiment, the electronic device may include a first sensor associated with the electronic device wherein the sensor produces a first signal indicative of an interaction between the person and the electronic device. Additionally, embodiments of the electronic device may include a processor connected to the sensor to receive the first signal from the sensor and produce data indicative of the person's use of the electronic device. Furthermore, the electronic device may include a transmitter to receive the data from the processor and produce a data signal encoded with the data.

An embodiment of a method of monitoring and evaluating the cognitive ability of a person is also disclosed herein. In an embodiment, at least one appliance is distributed in the domicile of the person. The appliance may include circuitry for sensing the person's interaction with the appliance and transmitting the interaction data. Embodiments of the method may further include the step of receiving the interaction data and analyzing the interaction data to produce first statistics representative of the person's interaction with the appliance. Finally, the embodiment of the method may include the step of evaluating the patient's cognitive ability based on the first statistics.

These and other advantages and features will become more readily understood from the following detailed disclosure that is provided in connection with the accompanying drawings.

DETAILED DISCLOSURE

Figure 1:
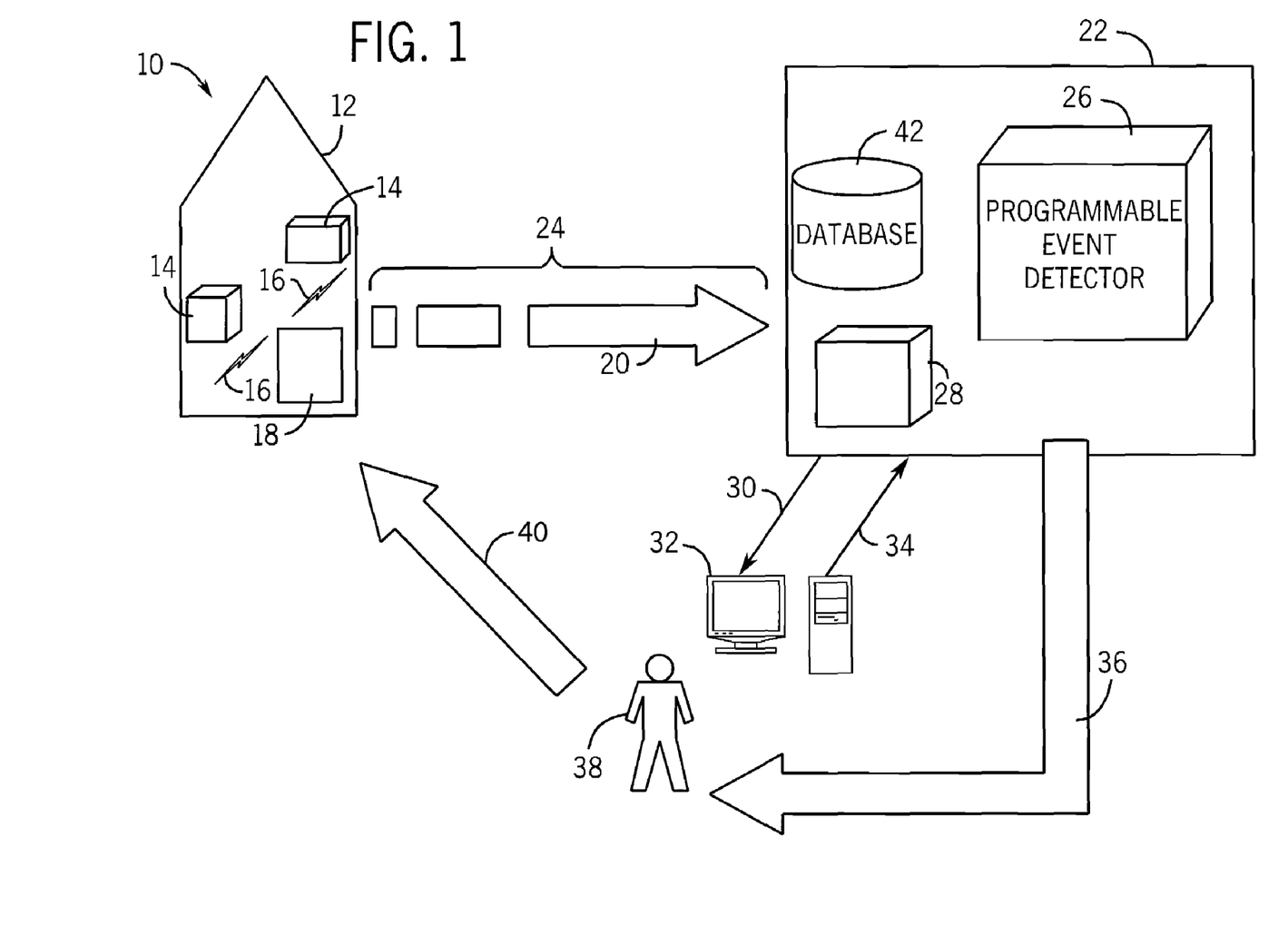
FIG. 1 is a schematic view of an embodiment of a system for remotely monitoring the activity of a person.

FIG. 1 depicts an activity monitoring system 10 that includes one or more activity sensors 14 distributed throughout a home 12. The activity sensors 14 produce communication signals 16 that may be transmitted via wireless or wired communication techniques to a communications relay 18.

The sensors 14 may include motion sensors located in connection with doors, cabinets, appliances, or any other sensors or sensor locations that are suitable for collecting and communicating data regarding the activities undertaken by the person in the home 12. Other suitable sensors 14 may include hazard sensors and/or security sensors.

In the event that one or more of the sensors 14 detects an unusual occurrence, intervention in the home 12 may be undertaken through a communication with the patient at the home from a location outside of the home, such as via a telephone call. Alternatively, a visit from a caregiver 38 or other suitable person, such as an emergency response professional, relative, or guardian may be initiated.

The communications relay 18 communicates the sensor data, or data points, collected from the sensors 14 by sending a data signal 20 containing the data to a remote monitoring center 22 by way of a suitable wired or wireless communications platform 24, such as, for example, wired telephone, wireless telephone, two-way walkie-talkie, pager, cable, the internet, or any other wireless communication platform. Depending upon the communication platform 24 chosen, the data signals 20 may be sent in near real-time or may be sent at discrete, regular or irregular intervals. For example, data signals 20 may be sent in near real-time via wireless telephone, two-way walkie-talkie, pager, cable, the internet or any other wireless communication platform. For a wired telephone communication platform, the data signals 20 may be buffered and transmitted at various time intervals.

The remote monitoring station 22, which is remotely located from the home 12, includes a database 42, a programmable event detector 26, and a status report generator 28. The database 42 serves as a collection device for the sensor data communicated via the signals 20. Upon a request from the caregiver 38 for a status report, the sensor data is forwarded from the database 24 to the status report generator 28. The status report generator 28 communicates a status signal 30 to a computer workstation 32 of the caregiver 38. The status signal 30 may, in some embodiments, be near real-time which is meant to include the transmission of signals anywhere in the range of almost instantaneously to up to and beyond three minutes. For example, for a two-way page communication platform 24, the amount of time required for the communication can be between two and three minutes. The status report generator 28 may be programmed to update the report for each home 12 at a certain interval, such as, for example, every ten minutes. The status signal 30 may include a report generated by the status report generator 28. The format and substance of the report may be dependent upon the request of the caregiver 38. It should be appreciated that the signal 30 can instead be communicated to and from a personal digital assistant (PDA) or other smart device instead of through the computer workstation 32.

The caregiver 38 may also select certain activities, that, if they occur in the home 12, would be considered an event. An event, in general, would include an activity or any important transition occurrence, such as a state transition (the change from one state to another, such as, for example from active to quiet) of which a caregiver 38 would want to be appraised. For example, the time of person wake up, an unusually long period of quiet or non-activity, or the use of an exterior door may be considered an important activity or state transition occurrence. The caregiver 38 communicates the parameters of what constitutes an event to the remote monitoring center 22 via a signal 34. While the caregiver 38 may not be granted the ability to define what constitutes an event, the caregiver 38 may be allowed to select activities or actions that constitute an event from a set of predefined activities. Further, in embodiments, the caregiver 38 may set the parameters to configure the events to match the normal activity of the patient in the home 12. For example, the caregiver 38 does not define what constitutes, for example "wake up," but the caregiver 38 can define when "wake up," would be considered late. The sensor data is stored and processed in the monitoring center 22. If the data indicates the occurrence of an event, a signal 36 may be sent to the caregiver 38 via any suitable communication medium, such as, for example, wired or wireless telephone, PDA, smart device, two-way walkie-talkie, email, or other internet supported communications media, such as, for example, through a pop-up announcement format. The caregiver 38 is then provided the opportunity to open a communication pathway 40 with the person residing in the home 12. The communications pathway 40 may be through a wired or wireless telephone line, and internet browser (i.e., e-mail or other internet-based communication tool), cable, PDA, or other smart device. Alternatively, the communication pathway 40 may be a visit in person by the caregiver 38 or another suitable person.

The activity monitoring system 10 makes use of the activity sensors 14 to monitor the activity of the person within the home 12. In addition to the regular status signal 30 sent to the caregiver 38, the programmable event detector 26 of the remote monitoring station 22 also analyzes the patient data stored in the database 42 such that a signal 36 is generated to alert the caregiver 38 when abnormal activity has been detected.

Thus, the activity monitoring system 10 as disclosed above presents an effective system by which a person's activity may be monitored to provide timely alerts to a caregiver 38 remotely located from the home 12. It should be noted that while the word home is used in the above description, such use in intended to include any type of domicile of the patient, and is not limited to a single family structure. As such, the use of the term home may also include a condominium or apartment, a co-op or other multiple person living arrangement, or one or more rooms of a nursing home within which the person lives.

Figure 2:
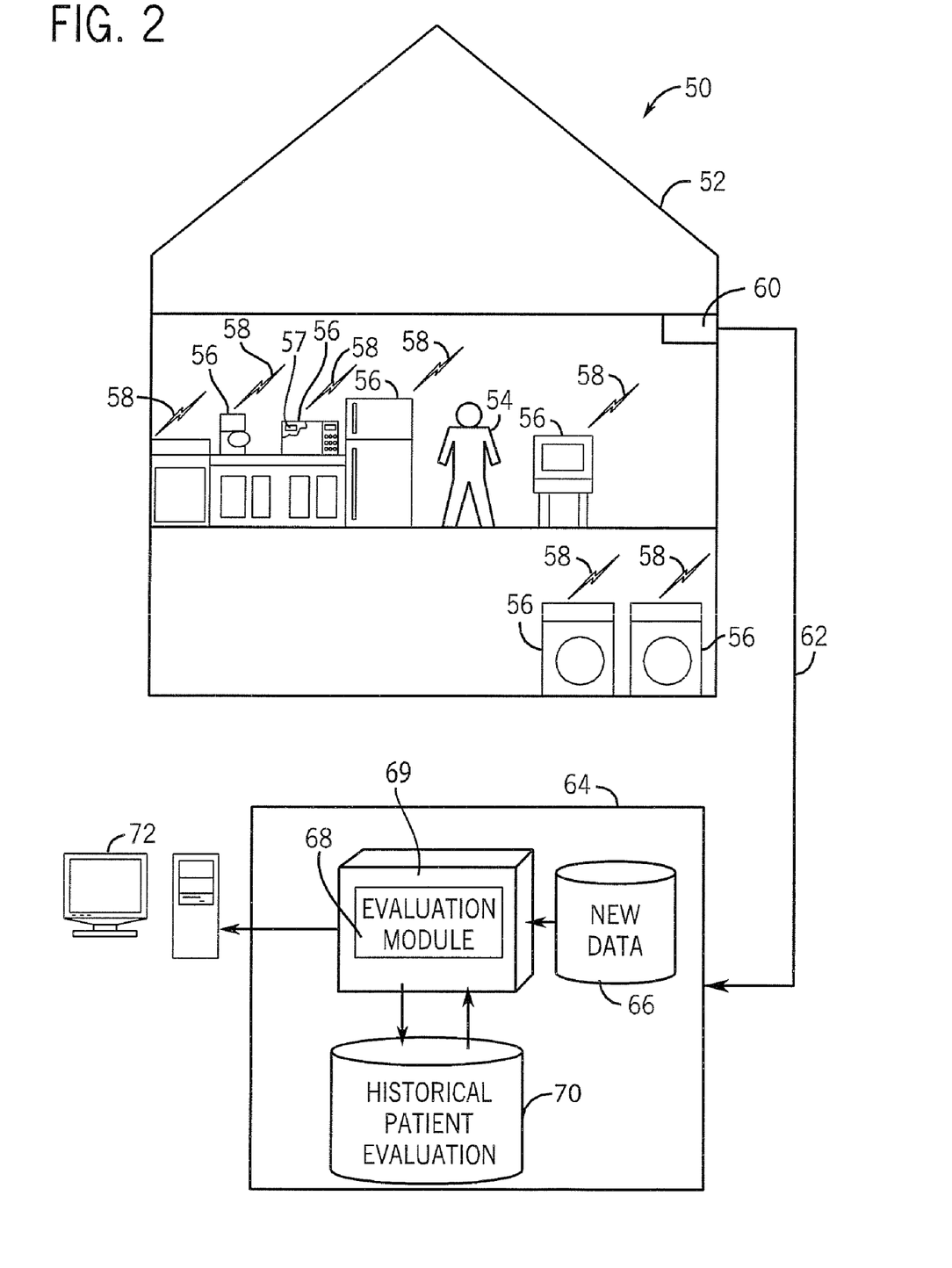
FIG. 2 is a schematic view of an embodiment of a system for monitoring the cognitive ability of a remotely located person.

While the activity monitoring system 10 provides the caregiver 38 with a timely notification of an emergency situation whereby care or additional contact with the patient is necessary, it is also desirable to be able to monitor and determine the mental or cognitive state of an independently living person using a monitoring system. FIG. 2 depicts an embodiment of a cognitive ability monitoring system 50. The monitoring system 50 includes the domicile 52 of a person 54. It should be noted that, as above, the domicile 52 should not herein be limited to that of a single family residence, but rather should be interpreted in an expansive sense to include any type of residence, including single family, apartments or condominiums, cooperative or group homes, or nursing home rooms, within which the patient 54 may reside.

The domicile 52 may include a plurality of electronic devices 56 distributed throughout the domicile 52. The electronic devices 56 may in some embodiments include appliances as may be commonly found in typical domiciles. A non-limiting exemplary list of appliances that may be considered to be within the scope of the electronic devices 56 may include a stove, coffee pot, microwave, refrigerator, washing machine, and/or dryer. Other electronic devices 56 may include that of a television or radio.

Figure 3:
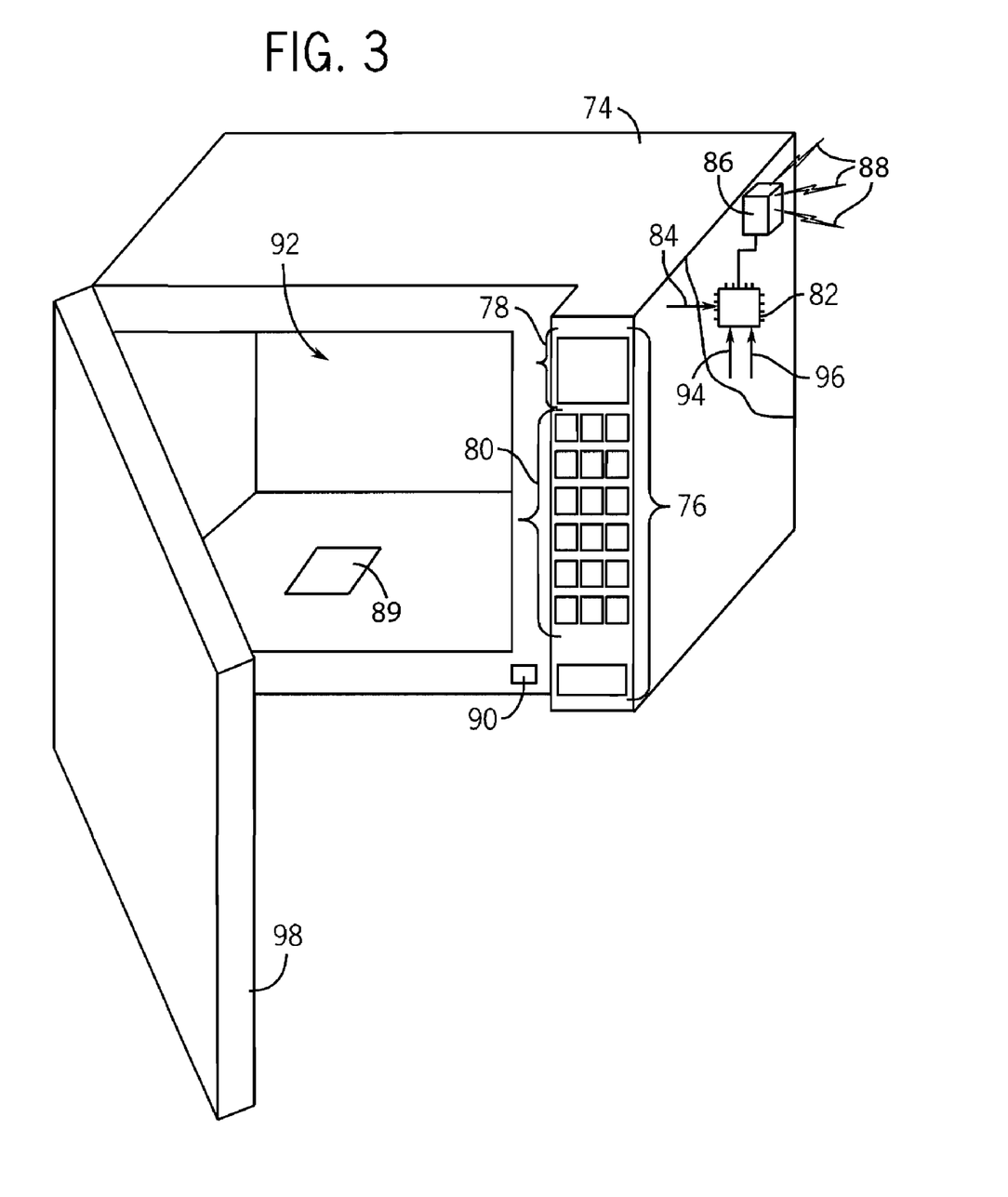
FIG. 3 depicts an embodiment of an appliance as may be used in conjunction with an embodiment of the system or method disclosed herein.

Each of the electronic devices 56 includes a processor 57, which will be described in greater detail herein with respect to FIG. 3. The processor 57 processes signals that are indicative of the use of the electronic device 56 by the patient 54. The electronic devices 56 each produce a data signal 58 that includes data regarding the use of the electronic device 56 by the person 54, as will be detailed further herein. The data signal 58 may be transmitted via a wired or wireless connection, as is most suitable for implementation of the system 50. The data signal 58 is received and/or processed by a communications relay 60 located somewhere in association with the domicile 52. The communications relay 60 may be placed at a location central to each of the electronic devices 56, or may be placed at a location within the domicile 52 such as to facilitate the transmission of data. The communications relay 60 receives the data signals 58 from the electronic devices 56 and processes the data and transmits the data via a combined data signal 62 to a remote monitoring station 64.

In some embodiments, the communications relay 60 may perform signal processing on the received data signals 58 to filter and/or digitize the received data signals 58 and to create the combined data signals 62. Alternatively, the communications relay 60 may simply combine the data signals 58 to form the combined data signal 62. Otherwise, the communications relay 60 may multiplex the received data signals 58 to be transmitted as a combined data signal 62.

In an alternative embodiment, the data signals 58 are transmitted directly to the remote monitoring station 64. This technique may be used if the remote monitoring station 64 is in a close enough proximity to the domicile 52, such as in a nursing home or assisted living facility, or in the event that the data signals 58 are transmitted from the electronic devices 56 using Internet-based data connection.

Once the combined data signal 62 is received by the remote monitoring station 64, the data from the combined data signal 62 is stored in a database 66 of raw electronic device data. The raw electronic device data is stored in the database 66 until a time when it may be processed by an evaluation module 68. As disclosed further herein, the evaluation module 68, or any other module, is operable on a computer processor, such as computer processor 69 of the monitoring station. The processor 69 is communicatively connected to databases 66 and 70, and executes the computer readable code of the evaluation module 68 to perform the functions disclosed in greater detail herein.

The evaluation module 68 processes the data from the electronic devices 56 that is stored in the database 66. The evaluation module 68 initially processes the signals received in order to develop a base line determination of the usage of each of the electronic devices 56 by the person 54. The baseline is used as identifying the standard or normal use of the electronic devices by the patient and will typically be arrived at by analyzing data collected over a period of time such as a day, a week, a month, or a plurality of months. This baseline determination is recorded in a database of historical evaluations 70. The database of historical evaluations 70 enables the later comparison of the baseline or normal electronic device usage versus a newly derived evaluation of the patient's electronic device usage as determined by the evaluation module 68. Thus a comparison between evaluations performed at different times may yield information regarding any decline in cognitive ability of the person. These determinations are then reported from the monitoring station 64 to a computer workstation 72 of a clinician charged with caring for and monitoring the patient 54.

The data signals 58, representing the person's use of the electronic device, will be described more fully herein with respect to FIG. 3, which depicts an exemplary embodiment of an electronic device in accordance with the system disclosed herein. In the embodiment depicted in FIG. 3, the electronic device 56 is a microwave appliance 74. The microwave 74 includes a user interface 76 that further includes a display 78 and a plurality of buttons and/or controls 80. The person operates the microwave 74 in a normal fashion, such as the person would operate any microwave appliance. The person programs the microwave function using the controls 80 to input typical commands such as energy level and cooking time. The person may then view an output of the entered function on the display 78.

The microwave 74 as presently disclosed deviates from a standard microwave in that the microwave 74 further includes a processor 82 that receives inputs 84 from the user interface 76. The inputs 84 from the user interface go beyond those inputs required to operate the microwave 74, and include an indication of the way the user interface 76 is operated by the person. These inputs 84 may include information regarding the time of day that the microwave 74 is used and the specific buttons or controls 80 that are activated during the person's use. Information regarding the person's use of the controls 80 that may be included in inputs 84 may include the order of the selection/activation of each of the controls and/or the timing of the delay between the person's selection of each of the controls 80. All of these inputs 84 are sent to the processor 82 which may further process the inputs 84, or may directly send along the inputs 84 to a transmitter 86 that produces a data signal 88.

Next, the microwave 74 may include additional sensors such as a pressure sensor 89 or an activity sensor 90. These additional sensors may be used to provide additional inputs to the processor 82 that are representative of the actual use of the microwave 74 by the person. The pressure sensor 89 may be disposed within the workspace of the microwave 74 such that the pressure sensor 89 senses when an object is placed in the microwave 74. The workspace of an appliance, such as the workspace of the microwave 74, may refer to the portion of the appliance in which something is placed or processed.

An input 94 from the pressure sensor 88 is sent to the processor 82. An activity sensor 90 may be associated with a door 98 of the microwave 74 or another similar component of another appliance. The activity sensor 90 may then sense the operation of the door 98 and provide additional activity sensor inputs 96 to the processor 82. The pressure sensor input 94 and the activity sensor input 96 provided to the processor 82 provide an indication of the actual use of the microwave 74 by the person, as opposed to the user interface inputs 84 that are indicative of the person's operation of the user interface 76. Data from the user interface 76, pressure sensors 88, and/or activity sensor 90 are transmitted via the transmitter 86 to the remote monitoring station 64 (FIG. 2).

As described above, and as will be detailed further herein with respect to FIG. 2, the remote monitoring station 64 utilizes the combined data signals from one or more of the electronic devices 56 to perform an initial evaluation of the cognitive ability of the person. This evaluation of the cognitive ability of the person may look at features of the combined data such as the person's routine use of specific electronic devices 56, the length of time between input commands when operating an electronic device 56, the accuracy with which the person enters the commands into the electronic device 56 and/or the person's actual, proper use of the electronic device 56. The person's actual and proper use of the electronic device 56 is monitored by a comparison of the inputs from the pressure and activity sensors in comparison to the inputs from the user interface. This comparison will yield an indication, as with the example of the microwave 74, whether the person first properly loads the microwave and then properly programs the microwave to heat the object placed in the microwave. Proper operation will be contrasted with an example wherein no indication of loading the microwave is received, yet the microwave 74 is programmed and operated.

Differences in the person's use of each of the electronic devices 56 are recorded over time. Thus, a person's cognitive ability (or decline thereof), over a length of time may be evaluated as the person takes longer amounts of time to correctly operate an electronic device or begins to experience an increased number of instances wherein the electronic device is improperly operated.

Beyond the monitoring of cognitive decline over a length of time, the system 50 provides diagnostic information regarding the person's mental status. Instances wherein the person programs an electronic device, yet the pressure and/or activity sensors fail to detect the loading of an object into the workspace 92 (FIG. 3) of the electronic device, may indicate the onset of conditions such as dementia or Alzheimer's. Repeated, frequent use or ritualistic use of an electronic device provides an indication of other conditions, such as obsessive compulsive disorder.

Another source of anxiety regarding an independently living person is whether or not the patient is obtaining sufficient nutrition. Monitoring the person's use and operation of common food preparation appliances provides an indication as to whether the person is successfully preparing his/her own meals. This may be a subject about which the patient maybe elusive during an interview or during a house call. Embodiments presently disclosed provide the ability to obtain this additional medical data.

Figure 4:
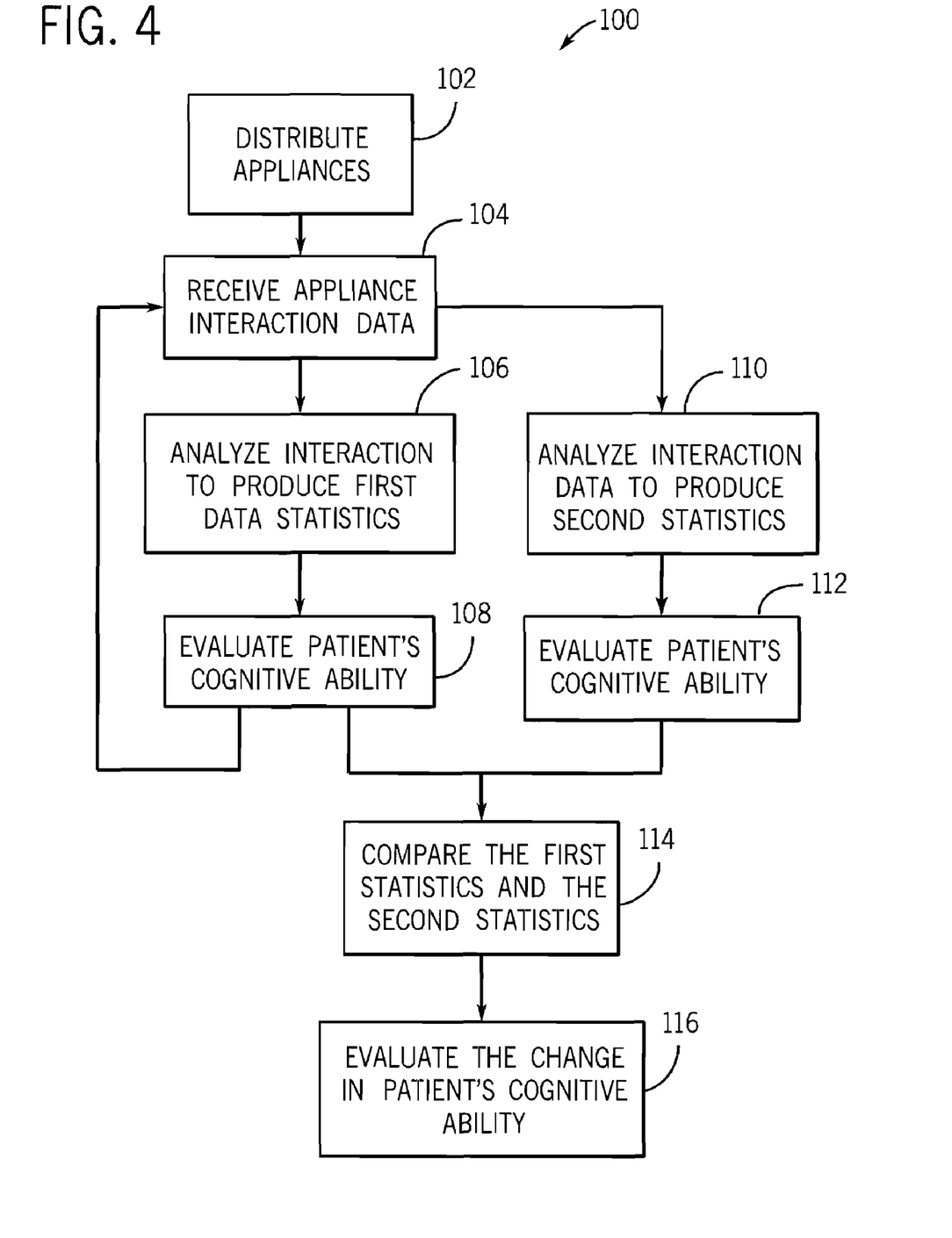
FIG. 4 is a flow chart depicting the steps in an embodiment of a method as disclosed herein.

Herein disclosed is also an embodiment of a method 100 of monitoring and evaluating the cognitive ability. FIG. 4 is a flow chart depicting the steps in an embodiment of this method 100. This embodiment of the method 100 begins at step 102 where a plurality of appliances are distributed throughout the domicile of the person. The appliances distributed in step 102 are appliances that are especially designed and fitted with additional sensors, such that the appliances monitor the interaction of the person with the appliance. Examples of such appliances distributed in step 10 have been disclosure herein in further detail. Next, at step 104, appliance interaction data is received. The appliance interaction data may be that data as recorded by the sensors as described above with respect to step 102, or may be other appliance interaction data as would be recognized by one skilled in the art. The appliance interaction data is received in step 104 via the wired or wireless transmission of a data signal from the plurality of appliances.

The received appliance data is then analyzed in step 106 to produce first statistics regarding the person's interaction with the appliance. The first statistics produced in step 106 may include, but are not limited to, such statistics as the rate at which the appliance is correctly loaded or unloaded, a measure of the instances of incorrect interaction order, the overall interaction duration, the time between specific events in the person's interaction with the appliance, and/or the frequency with at which the person interacts with the appliance.

The first statistics produced in step 106 are then used in step 108 to evaluate the person's cognitive ability. The person may be evaluated in step 108 to be of normal cognitive ability, or may be evaluated to have a pre-existing condition of a diminished cognitive ability. Alternatively, the evaluation in step 108 can include the determination of a baseline or "normal" level from an analysis of the first statistics from step 106. This baseline determination may be used in later analysis under alternative embodiments of the method.

In one such alternative embodiment, after a first evaluation of the person's cognitive ability has been made in step 108, the method returns to step 104 to receive additional appliance interaction data. This step may take place an hour, day, month, or months later. The performance of this step typically occurs at regular intervals, or may occur when prompted to do so at the request of a monitoring clinician. Once the new appliance interaction data is received in step 104, then this interaction data is analyzed in step 110 to produce second statistics regarding the person's interaction with the appliance. The second statistics may be some or all of interpretation data as identified with respect to step 106. The second statistics are then used in step 112 to perform a new evaluation of the person's cognitive ability. Thus, this alternative embodiment produces new evaluation of the person's cognitive ability at regular intervals such that a responsible clinician can review these periodic evaluations.

In still a further embodiment, the evaluation of the person's cognitive ability produced in step 108, based on the first statistics, and the evaluation of the person's cognitive ability from step 112, based upon the second statistics, are compared in step 114. The comparison of the first and second statistics in step 114 may simply measure the growth or decline in any of the statistics produced in steps 106 or 110. This comparison of the first and second statistics in step 114 is then used in step 116 to evaluate any change in the person's cognitive ability. The change in the person's cognitive can be seen in and/or determined from a lengthening in the time of the interaction between the patient and the appliance, the increase in the rate in which the appliance is incorrectly loaded or unloaded, or an increase in the rate at which the appliance is incorrectly operated through the user interface. Additionally, the evaluation of the change in the person's cognitive ability in step 116 may also include the determination of any specific pattern in the person's interactions with the appliance. Although the aforementioned listings of evaluations that may be performed in step 116 are to be considered exemplary and not limiting on those evaluations that may be performed by one of skill in the art.

Embodiments of the system and method as disclosed herein provide the benefit of a system and method that will offer the non-invasive and remote monitoring of cognitive ability. This form of monitoring cognitive ability reduces costs that otherwise would have to be incurred by a nurse or other clinician physically visiting a person and relying upon observation and interviews with the person in order to determine cognitive ability. Additionally, the proper assessment of a person's cognitive ability can be made resulting in the proper placement of the person in a living situation that is commensurate with the person's cognitive abilities. These living placements may include independent living, assisted living, or nursing home care. The implementation of embodiments of the system and method as disclosed herein be provide a basis for the evaluation of the person's cognitive abilities and thus provide an additional tool in evaluating the proper living situation for the person.

A system and method of remotely monitoring the use of a plurality of electronic devices by a person as disclosed herein may also be beneficial as medically valuable data may be obtained from an independently living person that may be otherwise difficult to obtain. The person may be evasive or attempt to cover up failings or declines in cognitive performance because the person may be embarrassed or not want to lose his/her independence. This may lead to situations wherein nothing is detected until the condition manifests itself as a decline in the person's health, as may be the case in the example above of a person that is unable to adequately provide himself/herself with adequate nutrition. Thus embodiments of the system and method as disclosed herein may provide warning of the underlying causes or the onset of such medical problems.

Some of the embodiments of the system and method as disclosed herein may be implemented solely through the use of one or more computers or processing devices. These devices may use implementations such as computer modules and the application of algorithms to achieve the functions as disclosed herein. In these embodiments the technical effect of the computer implementation is that these embodiments the technical effect of the computer implementation is that of providing a clinician with a tool to evaluate the cognitive ability of a remotely located person, as well as an indication thereof.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent elements with insubstantial differences form the literal languages of the claims.

What is claimed is:

1. A system for monitoring a remotely located person, the system comprising:
    at least one electronic device, the electronic device including:
    a user interface that receives a series of inputs from the person wherein the series of inputs define the operation of the electronic device;
    a first sensor associated with the user interface of the electronic device to produce a first signal indicative of the series of inputs;
    a processor associated with the electronic device and connected to the first sensor to receive the first signal from the first sensor and produce data being indicative of the person's use of the electronic device; and
    a transmitter connected to the processor to receive the data from the processor and transmit a data signal encoded with the data;
    a remote monitoring station that receives the data from the at least one electronic device, stores the data and analyzes the data to produce an evaluation of a cognitive ability of the person wherein the cognitive ability is based upon a change in the series of inputs received by the user interface over time.

2. The system of claim 1 wherein the at least one electronic device is an electronic appliance located in a domicile of the person.

3. The system of claim 2 further comprising a communications relay associated with the domicile, the communications relay receiving the data signals from the at least one electronic appliance and producing a combined data signal comprising the data from each of the plurality of electronic appliances, the combined data signal being transmitted to the remote monitoring station.

4. The system of claim 1 wherein the electronic device further comprises:
    a workspace that receives an object and executes the functionality of the electronic device; and
    a second sensor associated with the workspace, the second sensor monitors an interaction between the person and the workspace.

5. The system of claim 4 wherein the second sensor produces a second signal indicative of the interaction between the person and the workspace of the electronic device that places the object in the workspace; wherein the processor receives the second signal from the second sensor and incorporates the second signal into the data indicative of the person's use of the electronic device.

6. The system of claim 5 wherein the second sensor is an activity sensor coupled to a door of the workspace, the activity sensor monitors the patient's operation of the door to access the workspace.

7. The system of claim 5 wherein the second sensor is a pressure transducer, the pressure transducer monitors the placement of the object in the workspace.

8. The system of claim 7 wherein the evaluation of the cognitive ability of the person by the remote monitoring station comprises evaluating the data indicative of the person's use of the electronic device according to a predetermined order of interactions between the person and the electronic device.

9. The system of claim 8 wherein the predetermined order comprises placing the object in the workspace and starting the electronic device.

10. The system of claim 9 wherein the remote monitoring station analyzes the data with a technique selected from a list comprising:
    an accuracy of the series of inputs received by the user interface, an accuracy of the person's use of the electronic device compared to the predetermined order, and a temporal length of the person's interactions with the device.

11. A system for monitoring and evaluating the cognitive ability of a remotely located person, the system comprising:
    a plurality of appliances distributed throughout the domicile of a person, each appliance including:
    a user interface that receives a series of inputs from the person, wherein the series of inputs define the operation of the appliance;
    a first sensor that monitors the series of inputs received by the user interface of the appliance and produces a first signal indicative of the series of inputs;
    a second sensor coupled to the workspace, the second sensor monitors an interaction between the person and the workspace, constituting the operation of the appliance, wherein the sensor produces a second signal indicative of the interaction;
    a first processor that receives the first and second signals and produces data indicative of the person's interactions with the appliance; and
    a transmitter that receives the data from the first processor and transmits a data signal encoded with the data;
    a communications relay that receives the data signals from each of the appliances and transmits a combined data signal comprising the data from each of the appliances; and
    a remote monitoring station that receives the combined data signal, and analyzes the combined data signal to produce an evaluation of the person's cognitive ability based upon a predetermined relationship between the series of inputs and the interaction between the person and the workspace.

12. The system of claim 11 wherein the transmission of the combined data signal is in near real time and the second processor analyzes the combined data periodically to produce periodic evaluations of the person's cognitive ability.

13. The system of claim 11 wherein the predetermined relationship is a specified order of inputs into the user interface and interactions with the workspace.

14. The system of claim 13 wherein the specified order comprises loading the workspace before starting the appliance.

15. A method of monitoring and evaluating the cognitive ability of a person, the method comprising the steps:
   distributing at least one appliance in the domicile of the person, the at least one appliance including a user interface that receives a series of inputs from the person, and circuitry that senses the person's interaction with the user interface and transmits user interface interaction data indicative of the person's interaction with the user interface;
   receiving the interaction data with a remote monitoring station;
   analyzing the interaction data with the remote monitoring station to produce first statistics representative of the person's interaction with the user interface; and
   creating a baseline cognitive ability for the patient based on the first statistics;
   receiving updated interaction data with the remote monitoring system.
   analyzing the updated interaction data to produce second statistics representative of the person's interaction with the user interface; and
   comparing the first statistics to the second statistics to produce an evaluation of a cognitive ability of the person with respect to the baseline cognitive ability.

16. The method of claim 15 wherein the steps of analyzing the interaction data and analyzing the updated interaction data include analyzing an accuracy of the series of inputs and the first and second statistics include a measure of a rate at which the series of inputs are correct.

17. The method of claim 15 wherein the steps of analyzing the interaction data and analyzing the updated interaction data include analyzing an order of the series of inputs in the person's interaction with the appliance and the first statistics include a measure of the instances of incorrect input order.

18. The method of claim 15 wherein the steps of analyzing the interaction data and analyzing the updated interaction data includes analyzing the timing of the series of inputs in the person's interaction with the appliance and the first statistics include an overall interaction duration and a time between specific inputs in the person's interaction with the appliance.

19. The method of claim 15 wherein the at least one appliance further comprises:
   a workspace configured to receive an object and perform the function of the appliance; and
   circuitry that senses an interaction between the person and the workspace and transmits workspace interaction data indicative of the person's interaction with the workspace;
   wherein the first statistics and the second statistics are further representative of the person's interaction with the workspace.

20. The method of claim 19 wherein the steps of analyzing the interaction data and analyzing the updated interaction data further include analyzing interactions between the person and the workspace, and the first and second statistics include a measure of a rate at which the workspace is correctly loaded or unloaded.

* * * * *

UNITED STATES PATENT AND TRADEMARK OFFICE
CERTIFICATE OF CORRECTION

PATENT NO. : 7,855,650 B2
APPLICATION NO. : 12/103275
DATED : December 21, 2010
INVENTOR(S) : David Duckert et al.

Page 1 of 1

It is certified that error appears in the above-identified patent and that said Letters Patent is hereby corrected as shown below:

On the Title Page:

Item (57), under "ABSTRACT", in Column 2, Line 4, delete "sensor" and insert -- sensor, -- therefor.

In the Claims:

In Column 9, Line 29, in Claim 1, delete "person" and insert -- person, --, therefor.

In Column 9, Line 44, in Claim 1, delete "person" and insert -- person, --, therefor.

In Column 11, Line 5, in Claim 15, delete "steps:" and insert -- steps of: -- therefor.

In Column 11, Line 22, in Claim 15, delete "system." and insert -- system; -- therefor.

Signed and Sealed this
Twentieth Day of November, 2012

David J. Kappos
*Director of the United States Patent and Trademark Office*